(12) United States Patent
Guo et al.

(10) Patent No.: US 11,315,254 B2
(45) Date of Patent: Apr. 26, 2022

(54) METHOD AND DEVICE FOR STRATIFIED IMAGE SEGMENTATION

(71) Applicant: Ping An Technology (Shenzhen) Co., Ltd., Shenzhen (CN)

(72) Inventors: Dazhou Guo, Bethesda, MD (US); Dakai Jin, Bethesda, MD (US); Zhuotun Zhu, Bethesda, MD (US); Adam P Harrison, Bethesda, MD (US); Le Lu, Bethesda, MD (US)

(73) Assignee: Ping An Technology (Shenzhen) Co., Ltd., Shenzhen (CN)

( * ) Notice: Subject to any disclaimer, the term of this patent is extended or adjusted under 35 U.S.C. 154(b) by 44 days.

(21) Appl. No.: 16/928,521

(22) Filed: Jul. 14, 2020

(65) Prior Publication Data
US 2021/0225000 A1 Jul. 22, 2021

Related U.S. Application Data

(60) Provisional application No. 62/962,277, filed on Jan. 17, 2020.

(51) Int. Cl.
*G06T 7/11* (2017.01)
*G06T 7/00* (2017.01)
(Continued)

(52) U.S. Cl.
CPC .............. *G06T 7/11* (2017.01); *G06N 3/0454* (2013.01); *G06T 7/0012* (2013.01); *G06T 7/12* (2017.01);
(Continued)

(58) Field of Classification Search
CPC ......... G06T 7/11; G06T 7/0012; G06T 17/00; G06T 2207/20084; G06T 2207/10081;
(Continued)

(56) References Cited

U.S. PATENT DOCUMENTS

| 11,100,647 | B2 * | 8/2021 | Nikolov | G06T 7/62 |
| 2021/0012505 | A1 * | 1/2021 | Yuille | G06T 7/0012 |
| 2021/0073612 | A1 * | 3/2021 | Vahdat | G06N 3/082 |

FOREIGN PATENT DOCUMENTS

WO WO-2018227105 A1 * 12/2018 ........... G06T 7/0016

OTHER PUBLICATIONS

Zhang et al. "Hierarchical Convolutional Neural Networks for Segmentation of Breast Tumors in MRI With Application to Radiogenomics." IEEE Transactions on Medical Imaging, vol. 38, No. 2, Feb. 2019, pp. 435-447 (Year: 2019).*

* cited by examiner

*Primary Examiner* — Jon Chang
(74) *Attorney, Agent, or Firm* — Anova Law Group, PLLC

(57) ABSTRACT

A method and device for stratified image segmentation are provided. The method includes: obtaining a three-dimensional (3D) image data set representative of a region comprising at least three levels of objects; generating a first segmentation result indicating boundaries of anchor-level objects in the region based on a first neural network (NN) model corresponding to the anchor-level objects; generating a second segmentation result indicating boundaries of mid-level objects in the region based on the first segmentation result and a second NN model corresponding to the mid-level objects; and generating a third segmentation result indicating small-level objects in the region based on the first segmentation result, a third NN model corresponding to the small-level objects, and cropped regions corresponding to the small-level objects.

18 Claims, 7 Drawing Sheets

(51) Int. Cl.
*G06N 3/04* (2006.01)
*G06T 7/12* (2017.01)
*G06T 17/00* (2006.01)

(52) U.S. Cl.
CPC .... *G06T 17/00* (2013.01); *G06T 2207/10081* (2013.01); *G06T 2207/20081* (2013.01); *G06T 2207/20084* (2013.01)

(58) Field of Classification Search
CPC ............ G06T 2207/20081; G06T 7/10; G06T 2207/20076; G06T 2207/30096; G06N 3/0454; G06N 20/00; G06N 3/082; G16H 30/40; G16H 50/20
See application file for complete search history.

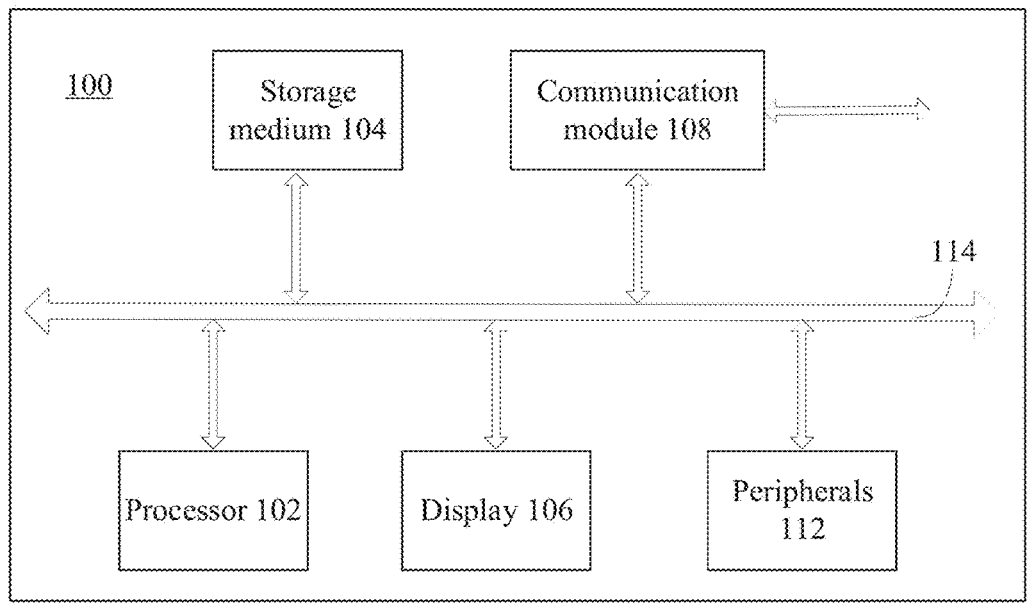

Obtaining a three-dimensional (3D) image data set representative of a region comprising at least three levels of objects
S202

Generating a first segmentation result indicating boundaries of anchor-level objects in the region based on a first neural network model corresponding to the anchor-level objects
S204

Generating a second segmentation result indicating boundaries of mid-level objects in the region based on the first segmentation result and a second NN model corresponding to the mid-level objects
S206

Generating a third segmentation result indicating small-level objects in the region based on the first segmentation result, a third NN model corresponding to the small-level object, and cropped regions corresponding to the small-level objects
S208

FIG. 2

METHOD AND DEVICE FOR STRATIFIED IMAGE SEGMENTATION

CROSS-REFERENCE TO RELATED APPLICATION

This application claims the priority of U.S. Provisional Patent Application No. 62,962,277, filed on Jan. 17, 2020, the entire contents of which are incorporated herein by reference.

FIELD OF THE DISCLOSURE

The present disclosure relates to the field of image processing technologies and, more particularly, relates to method and device for stratified image segmentation.

BACKGROUND

Raw image data may include multiple objects of various sizes and shapes that need to be individually segmented. Medical image data, such as a set of radiotherapy computed tomography (RTCT) images, may include multiple organs. Image segmentation, e.g., accurate identification of contours of these organs, is essential in performing diagnosis and treatment.

For example, head and neck (H&N) cancer is one of the most common cancers worldwide. High-precision radiation therapy such as intensity-modulated radiotherapy has been widely used for H&N cancer treatment because of its ability for highly conformal dose delivery. In this process, the radiation dose to normal anatomical structures, i.e. organs at risk (OARs), should be controlled to minimize post-treatment complications. This requires accurate delineation of tumors and OARs in RTCT images. Clinically, OAR segmentation is predominantly carried out manually by radiation oncologists. Manual delineation is not only time consuming (e.g. more than 2 hours for 9 OARs), but also suffers from large inter-practitioner variability. Unsurprisingly, with more OARs included, time requirements increase significantly, limiting the number of patients who may receive timely radiotherapy. These issues have spurred efforts toward automatic OAR segmentation in H&N cancer.

H&N OARs are, by their nature, 1) complex in anatomical shapes, 2) dense in spatial distributions, 3) large in size variations, and 4) low in RTCT image contrast. Existing methods either perform whole volume segmentation or segmentation-by-detection. However, since a great number of OARs need to be segmented, existing methods have difficulty in model optimization and do not have desired performance tailored to the challenging problem.

The disclosed method and system are directed to solve one or more problems set forth above and other problems.

BRIEF SUMMARY OF THE DISCLOSURE

One aspect of the present disclosure provides a method for stratified image segmentation. The method includes: obtaining a three-dimensional (3D) image data set representative of a region comprising at least three levels of objects; generating a first segmentation result indicating boundaries of anchor-level objects in the region based on a first neural network (NN) model corresponding to the anchor-level objects; generating a second segmentation result indicating boundaries of mid-level objects in the region based on the first segmentation result and a second NN model corresponding to the mid-level objects; and generating a third segmentation result indicating small-level objects in the region based on the first segmentation result, a third NN model corresponding to the small-level objects, and cropped regions corresponding to the small-level objects.

Another aspect of the present disclosure provides a device for stratified image segmentation. The device includes a memory and a processor coupled to the memory. The processor is configured to obtain a three-dimensional (3D) image data set representative of a region comprising at least three levels of objects; generate a first segmentation result indicating boundaries of anchor-level objects in the region based on a first neural network (NN) model corresponding to the anchor-level objects; generate a second segmentation result indicating boundaries of mid-level objects in the region based on the first segmentation result and a second NN model corresponding to the mid-level objects; and generate a third segmentation result indicating small-level objects in the region based on the first segmentation result, a third NN model corresponding to the small-level objects, and cropped regions corresponding to the small-level objects.

Another aspect of the present disclosure provides a non-transitory computer readable storage medium that has computer instructions stored thereon. The computer instructions can, when being executed by a processor, cause the processor to perform: obtaining a three-dimensional (3D) image data set representative of a region comprising at least three levels of objects; generating a first segmentation result indicating boundaries of anchor-level objects in the region based on a first neural network (NN) model corresponding to the anchor-level objects; generating a second segmentation result indicating boundaries of mid-level objects in the region based on the first segmentation result and a second NN model corresponding to the mid-level objects; and generating a third segmentation result indicating small-level objects in the region based on the first segmentation result, a third NN model corresponding to the small-level objects, and cropped regions corresponding to the small-level objects.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

FIG. 1 is a block diagram of an exemplary computing system according to some embodiments of the present disclosure.

FIG. 2 illustrates an exemplary stratified image segmentation process according to some embodiments of the present disclosure.

DETAILED DESCRIPTION

Figure 3:
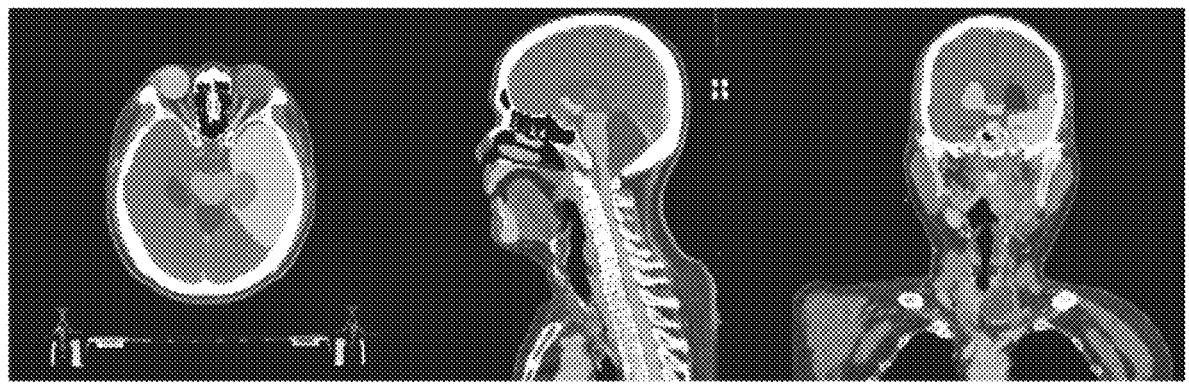
FIG. 3 illustrates two-dimensional (2D) views of sample RTCT images of head and neck region.

Reference will now be made in detail to exemplary embodiments of the invention, which are illustrated in the accompanying drawings. Hereinafter, embodiments consistent with the disclosure will be described with reference to the drawings. Wherever possible, the same reference numbers will be used throughout the drawings to refer to the same or like parts. It is apparent that the described embodiments are some but not all of the embodiments of the present invention. Based on the disclosed embodiments, persons of ordinary skill in the art may derive other embodiments consistent with the present disclosure, all of which are within the scope of the present invention.

The present disclosure provides a method and device for stratified image segmentation. In an exemplary embodiment, a three-dimensional (3D) image data set representative of a certain region may include multiple objects having various contrasts, sizes, and/or shapes. Some objects may have distinctive features or prominent sizes that facilitates easy segmentation, while other objects may have poor contrast and cause difficulty in the segmentation process. In the disclosed method, image segmentation is stratified. That is, objects may be divided into different categories/levels and segmentation are performed level by level using different strategies. In some embodiments, the easily-segmented category of objects may be segmented first and provide location references for the segmentation of other category(s) of objects. Additionally, tailored segmentation workflow based on neural network models are provided for different categories of objects.

FIG. 1 is a block diagram of an exemplary computing system/device capable of implementing the disclosed stratified image segmentation method according to some embodiments of the present disclosure. As shown in FIG. 1, computing system 100 may include a processor 102 and a storage medium 104. According to certain embodiments, the computing system 100 may further include a display 106, a communication module 108, additional peripheral devices 112, and one or more bus 114 to couple the devices together. Certain devices may be omitted and other devices may be included.

Processor 102 may include any appropriate processor(s). In certain embodiments, processor 102 may include multiple cores for multi-thread or parallel processing, and/or graphics processing unit (GPU). Processor 102 may execute sequences of computer program instructions to perform various processes, such as an image segmentation program, a neural network model training program, etc. Storage medium 104 may be a non-transitory computer-readable storage medium, and may include memory modules, such as ROM, RAM, flash memory modules, and erasable and rewritable memory, and mass storages, such as CD-ROM, U-disk, and hard disk, etc. Storage medium 104 may store computer programs for implementing various processes, when executed by processor 102. Storage medium 104 may also include one or more databases for storing certain data such as image data, training data set, testing image data set, data of trained neural network model, and certain operations can be performed on the stored data, such as database searching and data retrieving.

The communication module 108 may include network devices for establishing connections through a network. Display 106 may include any appropriate type of computer display device or electronic device display (e.g., CRT or LCD based devices, touch screens). Peripherals 112 may include additional I/O devices, such as a keyboard, a mouse, and so on.

In operation, the processor 102 may be configured to execute instructions stored on the storage medium 104 and perform various operations related to a stratified image segmentation method as detailed in the following descriptions. An input of the computing system 100 may be a to-be-segmented image data set representative of a region containing multiple objects, and an output may include a prediction result of each voxel in the image data set about a probability of the voxel belonging to each of the multiple objects.

Embodiments directed to stratified segmentation of organs at risk (OARs) on image data in head and neck region are described throughout the present disclosure as an exemplary illustration of the disclosed method and device. It can be understood that the disclosed method and device are also applicable in other image segmentation fields, such as medical images of other body regions and/or other specimens.

FIG. 2 illustrates an exemplary stratified image segmentation process 200 according to some embodiments of the present disclosure. The process 200 may be performed by any suitable computing device/server having one or more processors and one or more memories, such as computing system 100 (e.g. processor 102).

As shown in FIG. 2, a 3D image data set representative of a region may be obtained (S202). The 3D image data may include a plurality of voxels indicating intensities (e.g., grayscale values or color values) at corresponding 3D locations. The 3D image data set may be formed based on a stack of two-dimensional (2D) image slices. For example, the 2D image slices may be cross-sectional images taken around a single axis of rotation, and along a same longitudinal axis at fixed intervals.

FIG. 3 illustrates 2D views of sample RTCT images of head and neck region including multiple OARs with various contrasts, sizes, and shapes. A top view, a side view, and a front view are shown with delineated boundaries of multiple organs. The RTCT images may be obtained from a CT scan, which is a 3D image data set representative of the head and neck region.

Figure 4:
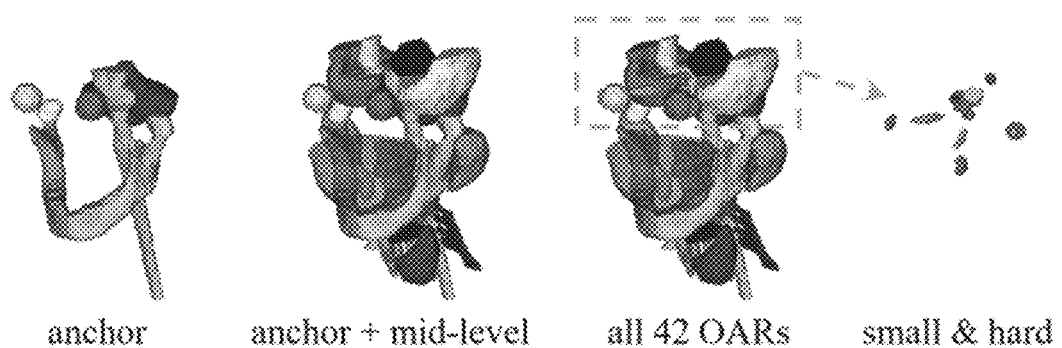
FIG. 4 illustrates three-dimensional views of segmented organs corresponding to the RTCT images shown in FIG. 3.

The head and neck region typically includes 42 OARs. In some embodiments, the 42 OARs can be stratified to three levels: anchor-level OARs, mid-level OARs, and small-level OARs. FIG. 4 illustrates three-dimensional views of segmented organs corresponding to the RTCT images shown in FIG. 3. As shown in FIG. 2, the anchor-level OARs may include eyes, brain stem, and mandible, the mid-level OARs may include soft-tissue glands, and the small-level OARs may include cochleae and optical nerves. The sizes of the anchor-level and mid-level OARs are greater than the sizes of small-level OARs. In some embodiments, tailor-made analysis workflows are provided for each stratification (i.e., each level/category of objects), and the anchor-level OARs are served as support to segmentation of mid-level and small-level OARs.

In an exemplary embodiment, the disclosed method provides stratified learning strategy to employ different network architectures (e.g., neural network architecture for segmentation) directed to different categories of objects (e.g., OARs), given highly distinct natures of the categories, thereby improving the segmentation performance.

Returning to FIG. 2, a first segmentation result can be generated indicating boundaries of anchor-level objects in the region based on a first neural network (NN) model corresponding to the anchor-level objects (S204).

Anchor-level objects may refer to objects that are high in intensity contrast and low in inter- and intra-reader variability. Accordingly, anchor-level objects can be segmented first to provide informative location references for segmenting other categories of objects.

In some embodiments, the first NN model may be trained specifically for the anchor-level objects and used to identify boundaries of the anchor-level objects. In some embodiments, the first NN model corresponding to the anchor-level objects may be a progressive holistically-nested network (P-HNN) model.

In some embodiments, the prediction result of the first NN model (e.g., the first segmentation result) may include probabilities of each voxel belonging to any of the anchor-level objects. The probabilities corresponding to each voxel may be represented by a vector valued mask. For example, the size of the vector corresponding to each voxel is the same and is the number of possible objects. Each element in the vector corresponds to one of the objects and indicates whether the voxel belongs to the object. In one example, if a voxel is determined as belonging to one object, the element in the vector corresponding to the object is 1, and other elements in the vector is 0.

In some embodiments, the architecture of the first NN model may be determined according to an automatic neural architecture search (NAS) process. NAS formulation facilitates tailoring specific neural networks for segmenting stratified categories of objects. In some embodiments, differential NAS may be performed to evaluate all candidate architectures simultaneously during optimization, limiting feasible search spaces. For example, the candidate architectures may have different kernel sizes with combination of 2D, 3D, and pseudo 3D configurations. Other NAS methods may include processes that exploit reinforcement learning or evolutionary algorithms.

After the first segmentation result is obtained, a second segmentation result can be generated indicating boundaries of mid-level objects in the region based on the first segmentation result and a second NN model corresponding to the mid-level objects (S206).

Mid-level objects may refer to objects that are low in contrast, but not inordinately small. In some cases, the mid-level objects may have comparable sizes as the anchor-level objects. The anchor-level predictions (e.g., the first segmentation result) can provide additional input for mid-level segmentation as guidance and reference-based grounding. Location references and semantically-based cues from the first segmentation result can be combined to generate the second segmentation result. That is, the input for the second NN model (e.g., feature parameters) may include both the 3D image data and information extracted from the first segmentation result. When training the second NN model, prior knowledge (e.g., anatomical knowledge, expert opinions, experiences of oncologists/radiologists) may be collected to provide insights of defining and using location references and semantically-based cues, such as relative position relationship between an anchor-level object and a mid-level object. For example, in H&N region segmentation, spatial information of mandible (anchor-level organ) can be used in the localization of mid-level organs such as: oral cavity, submandibular, and parotid. The semantic information of eyes (anchor-level organ) can be used in identifying small & hard organs such as lacrimal glands. During the mid-level and S&H branch training, voxels representing partial or whole of one or more anchor-level OARs are observed in the training sample. For example, when segmenting the lacrimal glands, voxels representing the eyes identified in the anchor-level segmentation are included. As a result, there forms a semantic relationship between the lacrimal glands and eyes. This indicates, given the eye prediction from the anchor branch, the S&H model may boost the likeliness of segmenting lacrimal glands.

In some embodiments, the second NN model corresponding to the mid-level objects may be a P-HNN model specifically trained for the mid-level objects. In some embodiments, the network architecture of the second NN model is determined based on a NAS process directed to the mid-level objects. In some embodiments, the prediction result of the second NN model (e.g., the second segmentation result) may include probabilities of each voxel belonging to any of the mid-level objects.

Further, a third segmentation result can be generated indicating boundaries of small-level objects in the region based on the first segmentation result, a third neural network model corresponding to the small-level object, and cropped regions corresponding to the small-level objects (S208).

Small-level objects may refer to objects that are poor in contrast and small in size relative to the anchor-level and mid-level objects. Small-level objects may also be referred as small and hard (S&H) objects since these objects are more difficult to segment than the other two categories. Segmentation result of anchor-level objects (e.g., the first segmentation result) can be used to guide S&H segmentation.

In some embodiments, a detection followed by segmentation strategy is implemented for small-level objects, for managing the extremely unbalanced class distributions across the entire data volume. For example, center locations of the small-level objects are detected first based on location references provided by the first segmentation result, and segmentation of the small-level objects are performed on localized and zoomed-in regions (also referred as volumes of interest) based on the detected center locations. The third NN model is used to perform the segmentation of the small-level objects in the localized and zoomed-in regions based on the segmentation result of anchor-level objects. In some embodiments, the third NN model corresponding to the small-level objects may be a P-HNN model specifically trained for the small-level objects. In some embodiments, the network architecture of the third NN model is determined based on a NAS process directed to the small-level objects in the localized regions. In some embodiments, the prediction result of the third NN model (e.g., the third segmentation result) may include probabilities of each voxel belonging to any of the small-level objects.

In process 200, a first stratification dimension is distinct processing frameworks for three categories of objects. A second dimension of stratification is searching distinct architectures for NN models for each object category. In other words, the NN models used for segmenting different object categories may have different characteristics. In some embodiments, for each NN model, a suitable architecture can be identified through differentiable neural architecture search (NAS). For example, an automatic selection across 2D, 3D or Pseudo-3D (P3D) convolutions with kernel sizes of 3 or 5 at each convolutional block for each NN model may be performed in structure learning.

In some embodiments, deeply-supervised 3D P-HNN models may be adopted as the backbone for all three categories, which uses deep supervision to progressively propagate lower-level features to higher-levels ones using a parameter-less pathway. The 3D P-HNN models may be implemented for image data set formed by RTCT images. The NAS search for P-HNN models includes searching P-HNN blocks.

Figure 5:
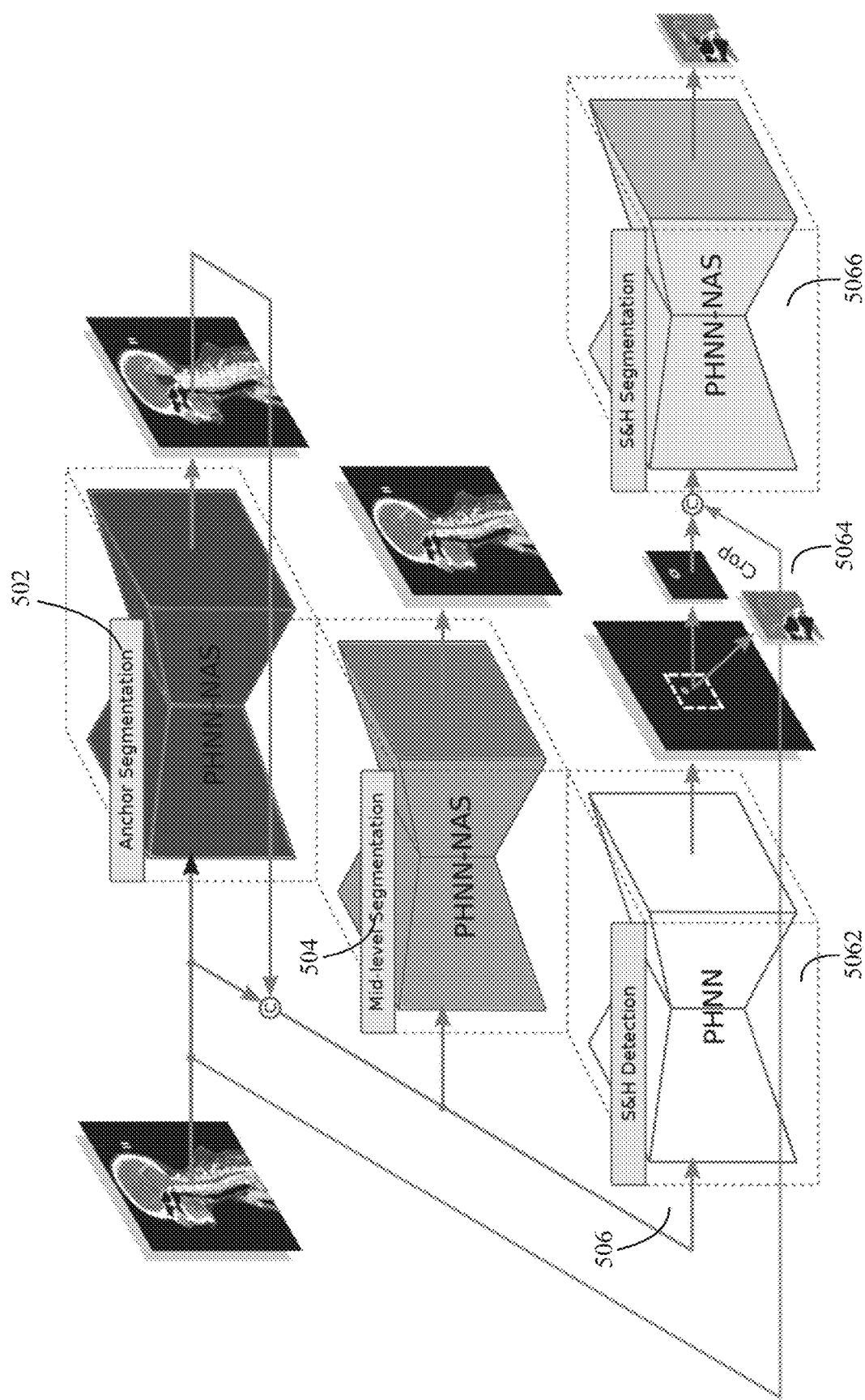
FIG. 5 is a block diagram illustrating an exemplary framework of stratified image segmentation according to some embodiments of the present disclosure.

FIG. 5 is a block diagram illustrating an exemplary framework 500 of stratified image segmentation according to some embodiments of the present disclosure. As shown in FIG. 5, the framework 500 includes three processing branches 502, 504, and 506 that respectively stratify anchor-level, mid-level, and small-level objects (e.g., OARs), and corresponds to S204, S206, and S208, respectively. The disclosed method/framework may be implemented on organ image segmentation, which may also be referred as stratified organ at risk segmentation (SOARS). According to an exemplary embodiment, a SOARS system first segments anchor-level OARs at branch 502, and then with the help of predicted anchor organs, mid-level and S&H OARs are segmented at branches 504 and 506. Each processing branches are implemented based on a corresponding neural network model.

The training data of the NN models may include N data instances and denoeted as $\mathbb{S}=\{X_n, Y_n^A, Y_n^M, Y_n^S\}_{n=1}^N$, where $X_n$ denotes nth 3D image data set (e.g., a set of RTCT images representative of head and neck region of subject n), $Y_n^A$ denotes ground-truth (GT) mask for anchor-level objects in nth data instance, $Y_n^M$ denotes ground-truth mask for anchor-level objects in nth data instance, and $Y_n^S$ denote ground-truth mask S&H OARs in nth data instance. The ground-truth masks may be obtained based on manual delineation performed by radiologists. Further, a test data instance, e.g., a to-be-segmented RTCT image data set, may be denoted as X, and $\hat{Y}^A$, $\hat{Y}^M$, and $\hat{Y}^S$ denote predicted masks for anchor-level, mid-level, and small-level objects, respectively. Additionally, $p^A(\cdot)$, $p^M(\cdot)$, and $p^S(\cdot)$ denote NN functions corresponding to anchor-level, mid-level, and small-level segmentations, respectively. $W^{(\cdot)}$ represents the NN parameters corresponding to the three categories of NN models. Hereinafter, when appropriate, n may be dropped in expressions for clarity; boldface characters are used to denote vector-valued volumes; and vector concatenation is considered as an operation across all voxel locations.

Assume there are C classes (e.g., number of anchor-level objects contained in the region, such as 9 classes of anchor-level organs in the head and neck and region), SOARS first uses the anchor branch 502 to generate the first segmentation result (e.g., OAR prediction maps) for every voxel location, j, and every output class, c, that belongs to the anchor-level objects:

$$\hat{Y}_c^A(j)=p^A(Y^A(j)=c|X;W^A), \hat{Y}^A=[\hat{Y}_1^A \ldots \hat{Y}_C^A],$$

where $\hat{Y}_c^A$ denote output segmentation map for class c. Here, predictions are vector valued 3D masks as they provide a pseudo-probability for every class. In other words, the output of the first NN model provides a prediction on whether each voxel of the 3D image data belongs to cth class, where c is any class of anchor-level OARs.

In some embodiments, anchor OARs have high contrast compared to surrounding tissue or are in easy-to-locate regions; hence, it is relatively easy to segment them directly and robustly based on pure appearance and context features. Consequently, they are desired candidates to support the segmentation of other OARs. In some embodiments, voxels identified as corresponding to anchor-level objects are excluded in the following prediction/segmentation processes directed to other object categories (e.g., mid-level and small-level objects).

Most mid-level OARs are primarily soft tissue, which have low contrast and can be easily confused with other structures with similar intensities and shapes. Direct segmentation can lead to false-positives or over/under segmentations. This can be addressed by using processing stratification to incorporate anchor predictions into mid-level learning, since the anchor predictions are robust and provide highly informative location and semantically-based cues. As shown in FIG. 5, at branch 504, the anchor predictions are combined with the input image data to create a multi-channel input for the second NN model. The multi-channel input can be denoted as [X, $\hat{Y}^A$]. Predictions can be made for each voxel location, j, and every output class c in the mid-level objects (e.g., 21 mid-level OARs in the head and neck region):

$$\hat{Y}_c^M(j)=p^M(Y^M(j)=c|X, \hat{Y}^A;W^M)$$

In this way, the mid-level branch leverages both the computed tomography (CT) intensities as well as the anchor OAR guidance, which can be particularly helpful in identifying regions with otherwise similar CT appearance. The mid-level predictions are collected into a vector-valued entity $\hat{Y}^M$. In some embodiments, voxels identified as corresponding to anchor-level or mid-level objects are excluded in small-level object segmentation.

Segmentation for the small and hard objects can be decoupled into a two-step process: detection followed by segmentation. Due to poor contrast and extremely imbalanced foreground and background distributions, directly segmenting the fine boundaries of S&H OARs from CT images may be very challenging when considering the entire volume. In contrast, the detection of center regions of S&H OARs is a much easier problem, since the H&N region has relatively stable anatomical spatial distribution. This means that the rough locations of S&H OARs can be inferred from the CT context with confidence. Once the center location is detected at branch 5062, a localized region can be cropped out at branch 5064, and segmenting the fine boundaries of the S&H OARs can be performed in a zoom-in fashion at branch 5066.

In some embodiments, heat map regression method can be adopted for detecting the center locations of the small-level objects. Heat map labels are created at each organ center using a 3D Gaussian kernel in training. Similar to the mid-level branch, the anchor branch predictions can be combined with the RTCT images as the detection input channels, to increase detection robustness and accuracy. Provided that $f(\cdot)$ denotes a neural network model such as P-HNN, the predicted heat maps for every S&H OAR $\hat{H}$ can be obtained by:

$$\hat{H}=f(X, \hat{Y}^A;W^D)$$

Given the resulting regressed heat map, the pixel location corresponding to a highest value may be selected as center location of a volume of interest (VOI). For example, in testing stage, an average mean 3D coordinate of the voxels that are above top-90 intensity value are predicted/identified as center location. The size of the VOI is greater than the maximum size of the OAR of interest, and may be for example, three-times the maximum size of the OAR of interest. The VOI is cropped from the original image data set and used as a base for fine segmentation of S&H OARS. As shown in FIG. 5, the output of center location detection can be concatenated with the cropped VOI as the input to the S&H OAR segmentation network:

$$\hat{Y}_c^S(j) = p^S(Y^S(j) = c|X, \hat{H}'; W^S)$$

It can be understood that the NN for segmenting S&H OAR operates on the cropped region/VOI.

In some embodiments, when training the neural network models, considering the significant variations in OAR appearance, shape, and size, SOARS may automatically search network architectures tailored to each categories of OARs, which adds an additional dimension to the stratification. For example, architecture of P-HNN used for each branch can be learned in a differentiable way.

Figure 6:
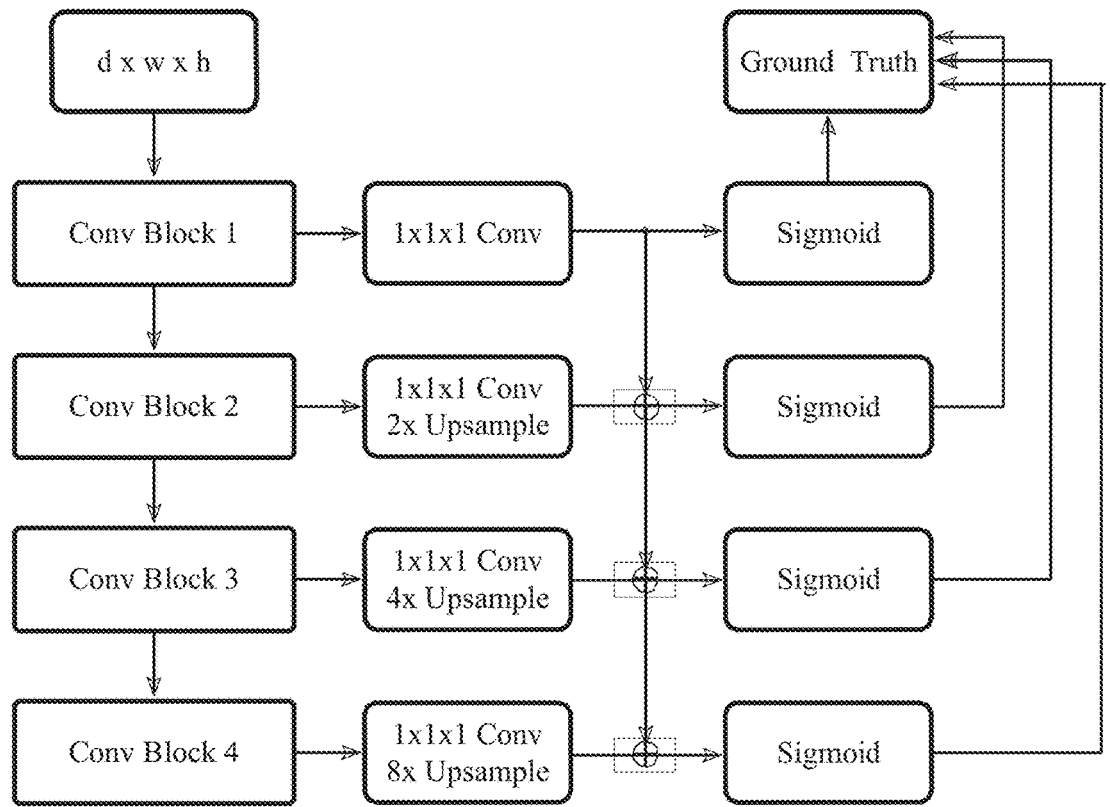
FIG. 6 is a diagram of a progressive holistically-nested network according to some embodiments of the present disclosure.
Figure 7:
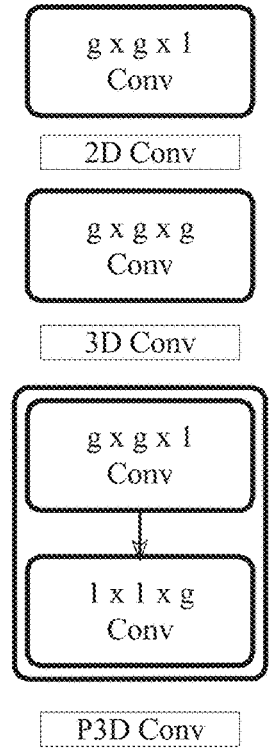
FIG. 7 illustrates a search space setting for network architecture search according to some embodiments of the present disclosure.

FIG. 6 is a diagram of a P-HNN model according to some embodiments of the present disclosure. FIG. 7 illustrates a search space setting for network architecture search according to some embodiments of the present disclosure. Referring to FIG. 6 and FIG. 7, let $\phi(\bullet; \omega_{x \times y \times z})$ denote a composite function of the following consecutive operations: batch normalization, a rectified linear operation and a convolution with an x×y×z dimension kernel. If one of the dimensions of a kernel is set to 1, it reduces to a 2D kernel. In some embodiments, a search space of possible architectures $\Phi$ may include, as shown in FIG. 7, 2D convolutions, 3D convolutions, or pseudo-3D convolution with different kernel sizes. For example, the kernel size may be 3 or 5 (e.g., g being 3 or 5 in FIG. 7), as shown below:
ti $\phi_{2D_3} = \phi(\bullet; \omega_{3 \times 3 \times 1})$ $\phi_{2D_5} = \phi(\bullet; \omega_{5 \times 5 \times 1})$ $\phi_{3D_3} = \phi(\bullet; \omega_{3 \times 3 \times 3})$ $\phi_{3D_5} = \phi(\bullet; \omega_{5 \times 5 \times 5})$ $\phi_{P3D_3} = \phi(\phi(\bullet; \omega_{3 \times 3 \times 1}); \omega_{1 \times 1 \times 3})$ $\phi_{P3D_5} = \phi(\phi(\bullet; \omega_{5 \times 5 \times 1}); \omega_{1 \times 1 \times 5})$ $\Phi = \{\phi_{2D_3}, \phi_{2D_5}, \phi_{3D_3}, \phi_{3D_5}, \phi_{P3D_3}, \phi_{P3D_5}\}$ In some embodiments, only one type of convolutional kernel is used to build each P-HNN convolutional block. Each convolutional block may include multiple convolutional layers. For example, if one convolutional block of a P-HNN model corresponding to one object category includes 6 convolutional layers, and the searched kernel is $\phi_x$, this indicates the kernels of all 6 convolutionally layers are $\phi_x$. In some embodiments, VGG16 network can be adopted as backbone network of the P-HNN model.

The search space can be made continuous by relaxing the categorical choice of a particular operation to a softmax over all possible operations (e.g., 6 possible convolution operations in the example shown above). The possible architectures/operations may be indexed and denoted by k, a set of learnable logits can be denoted as $\alpha_k$. Provided that parameter m is an iterator from 1 to 6 (i.e., 6 being a total number of possible architectures), a softmax can then be used to aggregate all possible architectures into one combined output, $\phi'$:

$$\gamma_k = \frac{\exp(\alpha_k)}{\sum_{m=1}^{6} \exp(\alpha_m)}$$

$$\phi' = \sum_{k=1}^{6} \gamma_k \phi_k$$

At a last step of the neural architecture search, the chosen network architecture of each block, $\tilde{\phi}$, can be determined by selecting the $\phi$ corresponding to the largest $\alpha_k$ value. Provided that the index corresponding to the maximum logit is denoted as $\tilde{k}$, then $\tilde{\phi} = \phi_{\tilde{k}}$. Provided that there are b blocks (such as 4 blocks as shown in FIGS. 6), and $\tilde{(\bullet)}$ denotes searched network architecture. The searched NN function can be represented as:

$$\tilde{p}(\bullet; \tilde{W}) = \tilde{\phi}^b(\tilde{\phi}^{b-1}(\ldots \tilde{\phi}^1(\bullet; \tilde{\omega}^1); \tilde{\omega}^{b-1}); \tilde{\omega}^b)$$

In some embodiments, NN models at each branch of SOARS are searched using the same strategy (e.g., branches 502, 504, and 5066).

Some examples demonstrating the performance of the forgoing method and device for stratified segmentation according to certain embodiments are presented in the following description. The examples focus on segmenting organs at risk based on RTCT images representative of head and neck region. Three performance evaluation criteria were used: Dice score (DSC) in percentage, Hausdorff distance (HD) and average surface distance (ASD) in millimeter (mm).

A sample dataset used for performance evaluation included 142 anonymized non-contrast RTCT images in H&N cancer patients, where 42 OARs are delineated during target contouring process for radiotherapy (hereafter referred to as H&N 42 dataset). Extensive 4-fold cross validation, split at the patient level, was conducted on the H&N 42 dataset to report results.

Each of the 142 CT scans is accompanied by 42 OAR 3D masks annotated by experienced oncologist(s). The average CT size is 512×512×360 voxels with an average resolution of 0.95×0.95×1.9 mm. The specific OARs stratification is as follows. Anchor OARs include 9 objects: brain stem, cerebellum, eye (left and right), mandible (left and right), spinal cord, and temporomandibular joint (left and right). Mid-level OARs include 21 objects: brachial plexus (left and right), basal ganglia (left and right), constrictor muscle (inferior, middle and superior), epiglottis, esophagus, hippocampus (left and right), larynx core, oral cavity, parotid (left and right), submandibular gland (left and right), temporal lobe (left and right), thyroid (left and right). S&H OARs include 12 objects: cochlea (left and right), hypothalamus, inner ear (left and right), lacrimal gland (left and right), optic nerve (left and right), optic chiasm, pineal gland, and pituitary.

An external dataset, public MICCAI2015 head and neck auto-segmentation challenge data1 (hereinafter referred as MICCAI2015) was also used for performance evaluation. This dataset has been extensively used by researchers to evaluate atlas and deep learning based H&N OAR segmentation. It contains 33 training cases and 15 test cases with 9 OARs annotated. The 9 OARs are: 2 anchor-level OARs including brain stem and mandible; 4 mid-level OARs including parotid (left and right) and submandibular gland (left and right); and 3 mid-level OARs including optic chiasm and optic nerve (left and right).

Image preprocessing were performed on the two data sets: H&N 42 dataset and MICCAI2015 data set. A windowing of [−500, 1000] Hounsfield unit (HU) was applied to every CT scan covering the intensity range of target OARs. For training data sets, VOIs sized at 128×128×64 were extracted from the windowed data set as training samples for the anchor and mid-level branches as well as the detection scheme in the S&H branch. The heat map labels in the detection scheme is a 3D Gaussian distribution with a standard deviation of 8 mm. The training VOIs were sampled in two manners: (1) 55 VOIs centered within each of the OARs were randomly extracted to ensure sufficient positive samples (e.g. 55 VOIs each including at least one OAR voxel and may or may not include an entire OAR); (2) additional 15 VOIs were sampled from the whole volume to obtain sufficient negative examples (e.g., 15 background VOIs that do not include any OAR voxel). This results in on average 70 VOIs per CT scan. The training data was further augmented by applying random scaling between 0.8 to 1.2. In testing, 3D sliding windows with sub-volumes of 128×128×64 and strides of 96×96×32 voxels were used. The probability maps of the sub-volumes are aggregated to obtain a whole volume prediction (e.g., the first, second, or third segmentation result), taking about average 20 seconds to process one input volume using a single GPU.

SOARS were implemented in PyTorch2, and trained on an NVIDIA Quadro RTX 8000. For network weight training, the batch size was set to 24. The initial learning rate for network weight training was set to 0.01 for the anchor and mid-level branches, and 0.005 for the S&H branch. All models were optimized with a momentum of 0.9 and a weight decay of 0.005. Dice score (DSC) loss is used for the segmentation task training. The S&H detection branch is trained using L2 loss with a 0.01 learning rate. The H&N 42 dataset were divided into four data sets: training set, weight-validation set, NAS-validation set, and testing set. The ratio of samples included in the training set, weight-validation set and NAS-validation set were 2:1:1. The network weights was trained using the training set and validated using the weight-validation set.

The detailed training strategy includes: the anchor-level branch were trained for 50 epochs. The parameters of the first NN model corresponding to the anchor branch was then fixed. The output of the anchor-level training were concatenated to the original RTCT data, together they are used in training the mid-level and S&H branches (i.e., the second and third NN models) for 50 epochs. Fine-tune of the whole pipeline in an end-to-end manner for 10 epochs were performed in the end.

For NAS of each NN model, the NAS parameter $\alpha_k$ were fixed for first 20 epochs of the 50 epochs. Then $\alpha_k$ and the network weights were updated for an additional 30 epochs. The batch size for NAS training was set to 2. Only data in the validation set were used for updating $\alpha_k$. The NAS was trained using the weight-validation set and validated using the NAS-validation set. The NAS parameter $\alpha_k$ is optimized using Rectified Adam (RAdam) optimizer. After NAS is completed, the searched network were retrained from scratch for 50 epochs with a batch size of 12. The initial learning rate for NAS was set to 0.005 for the anchor and mid-level branches NN models, and 0.001 for the S&H branch NN model.

Effectiveness of the stratification processing of SOARS were evaluated by comparing ablation results of baseline model, model specifically trained for a specific category based on only CT image data, and model trained for a specific category based on CT image data and NAS. The ablation studies were conducted using 1 fold of the dataset. For mid-level and S&H OARs, ablation result from model trained based on both CT image data and anchor OARs information was also evaluated. The quantitative results in these ablation studies used one fold of the data set. The performance was measured by DSC (unit: %), HD (unit: mm), and ASD (unit: mm).

TABLE 1

Anchor OARs

|  | DSC | HD | ASD |
| --- | --- | --- | --- |
| Baseline | 84.02 | 5.98 | 0.82 |
| CT Only | 84.14 | 5.25 | 0.79 |
| CT + NAS | 85.73 | 4.77 | 0.77 |

TABLE 2

Mid-level OARs

|  | DSC | HD | ASD |
| --- | --- | --- | --- |
| Baseline | 63.68 | 12.97 | 3.48 |
| CT Only | 67.31 | 12.03 | 3.97 |
| CT + Anchor | 70.73 | 10.34 | 1.67 |
| CT + Anchor + NAS | 72.55 | 9.05 | 1.31 |

TABLE 3

S&H OARs

|  | DSC | HD | ASD |
| --- | --- | --- | --- |
| Baseline | 60.97 | 4.86 | 0.98 |
| CT Only | 62.09 | 4.19 | 1.06 |
| CT + Heat map | 71.75 | 2.93 | 0.52 |
| CT + Heat map + NAS | 72.57 | 2.94 | 0.49 |

The ablation results for segmenting the anchor, mid-level and S&H OARs are shown in Tables 1-3, respectively. The baseline model used for comparison is 3D P-HNN model trained on all 42 OARs together. When anchor OARs are stratified to train only on themselves, there is a slight improvement as compared to the baseline model, consistent with the observation that anchor OARs generally have good contrast and are easy to optimize. However, when focusing on mid-level OARs, there is a marked DSC score improvement (3.6%) when only training on mid-level OARs instead of training on all. This demonstrates the disadvantage of segmenting a large number of organs together without considering their differences. When further adding anchor OAR predictions as support, both DSC scores and the ASD experience large improvements, i.e. from 67.3% to 70.7% in DSC and 3.97 to 1.67 mm in ASD. These significant error reductions indicate that anchor OARs serve as effective references to better delineate the hard-to-discern boundaries of mid-level organs (which are mostly soft-tissue).

Figure 8:
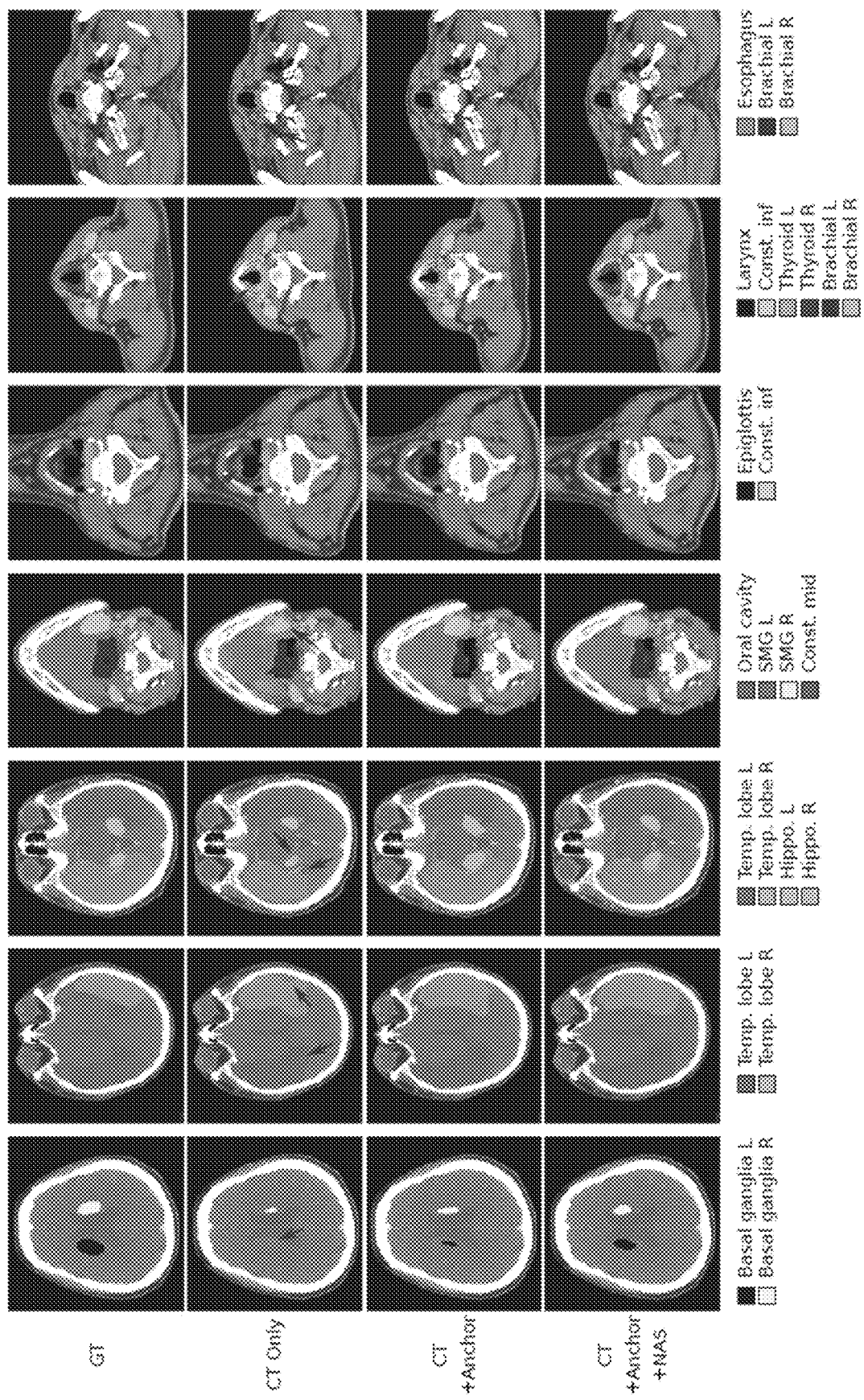
FIG. 8 illustrates qualitative examples of segmenting mid-level OARs using different setups according to some embodiments of the present disclosure.

FIG. 8 depicts qualitative examples of segmenting mid-level OARs using different setups according to some embodiments of the present disclosure. As shown in FIG. 8, seven columns are seven representative axial slices of RTCT images. Improvements are indicated by arrows. The first row are RTCT images with OAR delineations of a radiation oncologist. The second row shows segmentation result in RTCT images based on model trained on mid-level OARs using only CT image data. The third row shows the impact of incorporating information of anchor OARs, which can help the segmentation of soft-tissue mid-level OARs. The fourth row demonstrates the impact of NAS, indicating the necessity of adapting network architectures for different OARs. Segmentation results shown on the fourth row are closest to the standards shown in the first row, thus having the best performance. The segmentation performance of the third row is also visibly better than the second row.

Figure 9:
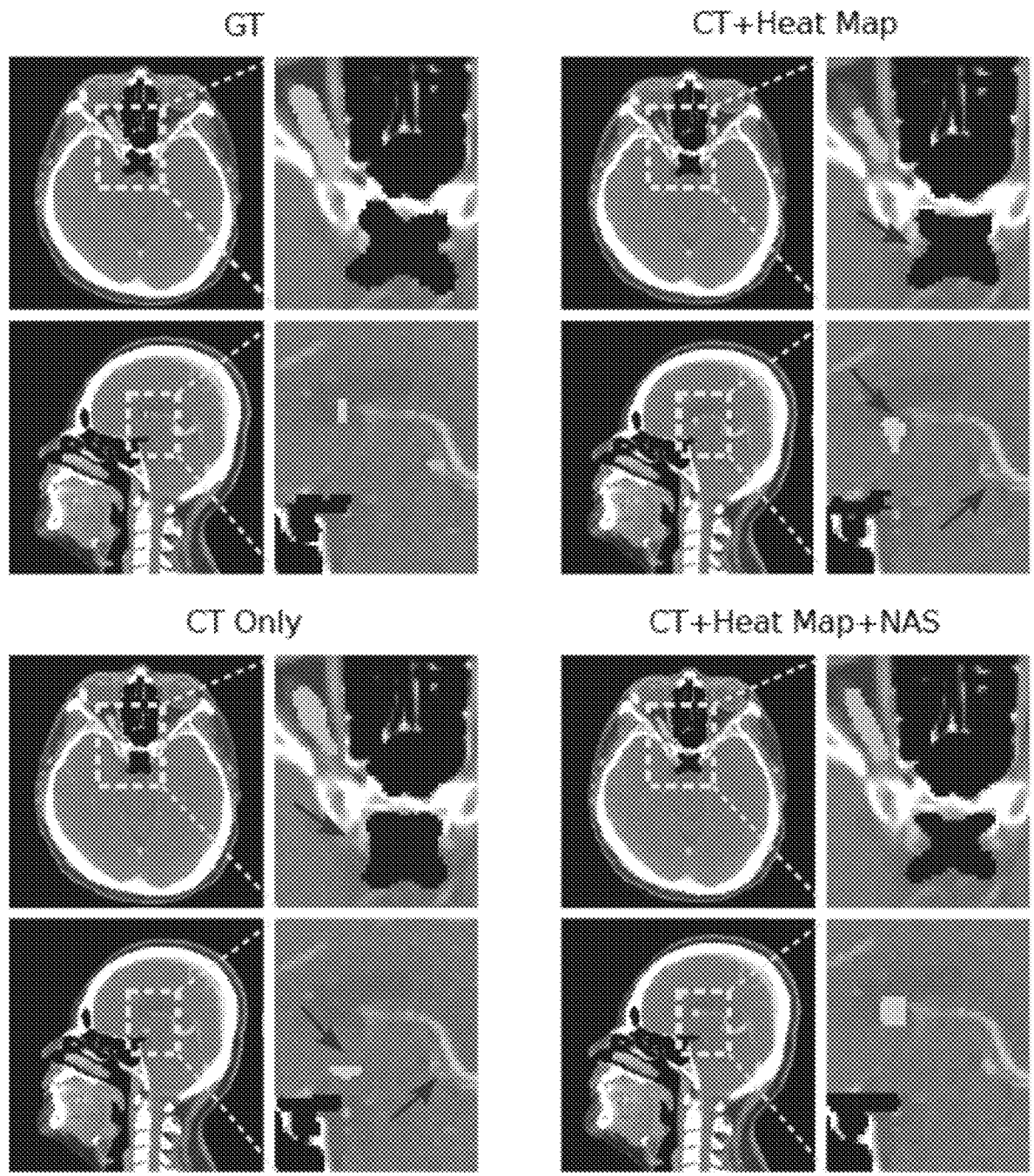
FIG. 9 illustrates qualitative examples of segmenting small-level OARs using different setups according to some embodiments of the present disclosure.

Regarding S&H OAR branch segmentation, the accuracy of using the detection-by-segmentation network to locate regressed center-points were evaluated. Both the regressed and ground-truth heat maps were binarized by keeping the top 1000 largest intensity voxels, and their corresponding HD were reported. Note, as cochlea is spatially enclosed by inner-ear, thus a single heat map, i.e. ear, were used for both OARs detection. Table 4 demonstrates that the center points of S&H OARs can be detected with high robustness. Table 5 reports category-by-category detection accuracy of the regressed center points using the detection-by- segmentation network. The average distances between regressed and true center points, as well as the Hausdorff distances between the binarized regressed and binarized true heat maps are measured. Lt is short for left and Rt is short for right. The best performance is highlighted in bold. An average HD reduction of 13.7 mm (from 18.9 mm to 6.2 mm) were achieved as compared to the detection using only RTCT images. The HD for all OARs are reduced, especially the lacrimal gland, optic chiasm, and pineal gland. These significant HD reductions indicate that the anchor OARs serve as effective references to better detect the S&H OAR locations. Moreover, when using the anchor OARs as support, the distance between regressed and true center points is smaller than the method based on CT data only, which shows improved performance. No S&H OAR was missed by the detection-by-segmentation strategy in conducted experiments, demonstrating the robustness of the disclosed detection-by-segmentation approach. In addition, the evaluated segmentation methods as shown in Table 3 were performed on predicted VOIs except the baseline model. By cropping the VOI based on the center point detection outcome, a remarkable improvement was shown in segmenting the S&H OARs, increasing DSC from 62.09% to 71.75%, as compared against the baseline model that performs direct segmentation on CT data. This further demonstrates the value of the disclosed processing-based stratification method, which provides for a desired treatment of OAR categories with different characteristics. FIG. 9 depicts qualitative examples of segmenting small-level OARs using different setups according to some embodiments of the present disclosure. For visualization purpose, dashed rectangles indicates enlarged area for illustrating segmentation results and highlighting improvements. As indicated using the arrows, the disclosed method achieves visually better segmentation on optic chiasm, hypothalamus, and pineal gland.

TABLE 4

|  | Dist (mm) |
|---|---|
| CT only | 3.25 ± 2.34 |
| CT + Anchor | 2.91 ± 1.74 |

TABLE 5

|  | Dist (mm) | | HD (mm) | |
|---|---|---|---|---|
|  | CT Only. | CT ± Anchor | CT Only. | CT ± Anchor |
| Ear Lt | 3.9 ± 2.5 | 3.9 ± 2.6 | 6.7 ± 3.3 | 5.7 ± 2.1 |
| Ear Rt | 1.9 ± 1.4 | 1.6 ± 1.0. | 4.4 ± 1.8 | 3.4 ± 41.3 |
| Hypothalamus | 2.6 ± 1.7 | 2.3 ± 41.5 | 4.0 ± 2.0 | 3.6 ± 41.5 |
| Lacrimal Gland Lt. | 5.6 ± 5.7 | 4.6 ± 3.1 | 28.0 ± 76.8 | 14.7 ± 20.7 |
| Lacrimal Gland Rt | 3.3 ± 1.9 | 3.0 ± 1.7 | 47.4 ± 112.0 | 4.7 ± 1.4 |
| Optic Chiasm: | 3.9 ± 2.5 | 3.4 ± 41.9 | 26.6 ± 71.8 | 10.6 ± 25.6 |
| Optic Nerve Lt | 2.5 ± 1.6 | 2.6 ± 1.5. | 4.6 ± 1.8 | 4.5 ± 1.20 |
| Optic Nerve Rt | 3.0 ± 1.2 | 3.1 ± 1.6 | 21.9 ± 61.0 | 4.91 ± 1.6 |
| Pineal Gland | 2.5 ± 2.5 | 1.84 ± 0.7 | 27.7 ± 72 2 | 3.9 ± 1.3 |
| Average | 3.3 | 2.9 | 18.9 | 6.24 |

Tables 1-3 also show performance improvements provided by NAS. As can be seen, all three branches trained with NAS consistently produce more accurate segmentation results than those trained with the baseline P-HNN network. This validates the effectiveness of NAS on complicated segmentation tasks. Specifically, the anchor and mid-level branches have considerable performance improvement, from 84.1% to 85.7% and 70.7% to 72.6% in DSC scores respectively, while the S&H branch provides a marginal improvement (0.8% in DSC score). For segmenting the S&H OARs, the strong priors of detected heat maps may have already made the segmentation task much easier. Nonetheless, besides the dramatic improvements already provided by the stratified approach, the fact that NAS is able to boost performance even further attests to its benefits. Some qualitative examples demonstrating the effectiveness of NAS are shown in last row of FIG. 3 and lower right part of FIG. 4. The searched network architectures (i.e., after completing NAS) for the anchor branch included 2D-kernel3, 2D-kernel5, 2D-kernel3 and 3D-kernel5 for the four convolution blocks. For the mid-level branch, they were 2D-kernel3, 2.5D-kernel5, 2D-kernel3 and 2.5D-kernel5. The result indicates that 3D kernels may not always be the best choice for segmenting objects with reasonable size, as mixed 2D or P3D kernels dominate both branches. Consequently, it is possible that much computation and memory used for 3D networks could be avoided by using an appropriately designed 2D or P3D architecture. For the S&H branch, the searched architecture was 2D-kernel3, 3D-kernel5, 2D-kernel3 and 3D-kernel5 for the four convolution blocks. As can be seen, more 3D kernels are used compared to the other two categories of OARs, consistent with the intuition that small objects with low contrast rely more on the 3D spatial information for better segmentation.

Comparison with other state-of-the-art methods including P-HNN , UNet, and UaNet were conducted. Using four-fold cross-validation, SOARS implementing the disclosed method were evaluated on a comprehensive H&N OAR dataset that includes 142 RTCT images with 42 annotated OARs. Comparison results by category are shown in Table 6.

It is demonstrated that both dimensions of the disclosed stratification, i.e. category-specific processing and NAS, significantly impact segmentation performance. An average DSC and HD of 75.14% and 6.98 mm were achieved, respectively, which corresponds to improvements of 7.51% and 2.41 mm, respectively over a non-stratified baseline method. Compared to a 3D Mask R-NN based UaNet method, SOARS produced improvements of 4.70% and 2.21 mm, in DSC and HD, respectively. SOARS achieves best performance in all metrics.

TABLE 6

|  |  | UNet | PHNN | UaNet | SOAR |
|---|---|---|---|---|---|
| Anchor OARs | DSC | 82.97 | 84.26 | 84.30 | 85.04 |
|  | HD | 8.90 | 6.12 | 8.89 | 5.08 |
|  | ASD | 1.06 | 1.18 | 1.72 | 0.98 |
| Mid-level OARs | DSC | 63.61 | 65.19 | 69.40 | 72.75 |
|  | HD | 11.06 | 13.15 | 11.57 | 10.10 |
|  | ASD | 1.92 | 2.97 | 2.06 | 1.66 |
| S&H OARs | DSC | 59.64 | 59.42 | 61.85 | 71.90 |
|  | HD | 6.38 | 5.23 | 5.28 | 2.93 |
|  | ASD | 1.31 | 0.82 | 1.53 | 0.53 |
| All | DSC | 66.62 | 67.62 | 70.44 | 75.14 |
| OARs | HD | 9.26 | 9.39 | 9.20 | 6.98 |
|  | ASD | 1.86 | 2.23 | 1.83 | 1.12 |

Table 7 reports category-by-category DSC of the disclosed SOARS against other three methods. Table 8 reports category-by-category HD of the disclosed SOARS against other three methods. Lt is short for left and Rt is short for right. Const. is short for constrictor muscle, SMG is short for submandibular gland, and TM joint is short for temporomandibular joint. For both metrics, SOARS achieved 30 out of 42 OARs best performance. SOARS performed slightly worse than UaNet on temporal lobe and temporomandibular joint segmentations in terms of DSC. Yet, the DSC differences are relatively small.

Figure 10:
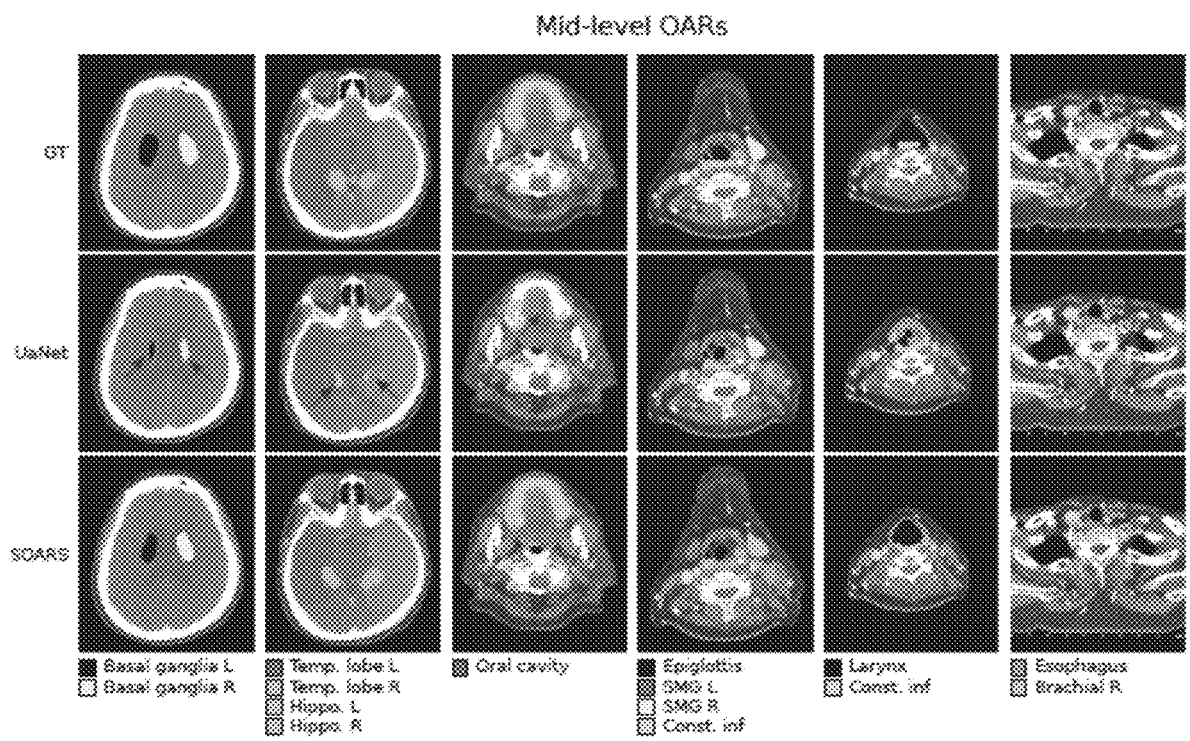
FIG. 10 illustrates comparisons of qualitative examples of segmenting mid-level OARs according to some embodiments of the present disclosure.
Figure 11:
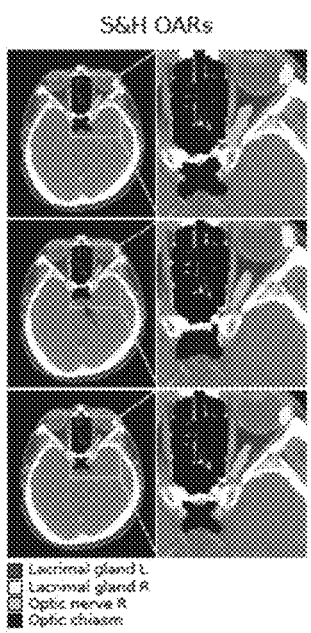
FIG. 11 illustrates comparisons of qualitative examples of segmenting small-level OARs using different setups according to some embodiments of the present disclosure.

In addition, FIG. 10 include qualitative illustrations of segmenting mid-level OARs using UaNet and the disclosed SOARS. FIG. 11 include qualitative illustrations of segmenting small-level OARs using UaNet and the disclosed SOARS. The two figures demonstrate that SOARS achieves visually better segmentation on mid-level and small-level OARs.

TABLE 7

| Organ | UNet | P-HNN | UaNet | SOARS |
|---|---|---|---|---|
| Basal Ganglia Lt | 64.0 ± 12.4 | 63.5 ± 16.6 | 63.6 ± 13.7 | 63.8 ± 13.7 |
| Basal Ganglia Rt | 64.7 ± 13.9 | 63.5 ± 14.2 | 67.4 ± 15.0 | 63.6 ± 11.6 |
| Brachial Lt | 59.8 ± 13.7 | 48.8 ± 11.8 | 49.9 ± 10.3 | 66.8 ± 17.1 |
| Brachial Rt | 58.8 ± 13.7 | 49.4 ± 7.0 | 53.5 ± 8.0 | 65.5 ± 14.2 |
| Brainstem | 81.7 ± 5.4 | 80.1 ± 6.8 | 80.6 ± 6.3 | 81.0 ± 5.7 |
| Cerebellum | 83.2 ± 2.7 | 88.8 ± 2.8 | 90.1 ± 2.8 | 90.2 ± 2.3 |
| Cochlea Lt | 64.0 ± 17.6 | 67.2 ± 10.4 | 66.5 ± 12.6 | 72.3 ± 12.2 |
| Cochlea Rt | 64.2 ± 10.0 | 67.2 ± 10.4 | 68.2 ± 12.6 | 69.5 ± 12.4 |
| Const. inf | 63.4 ± 17.1 | 61.8 ± 14.9 | 73.6 ± 10.6 | 65.0 ± 18.3 |
| Const. mid | 64.9 ± 15.4 | 63.1 ± 14.5 | 66.1 ± 11.3 | 66.9 ± 15.1 |
| Const. sup | 64.0 ± 10.2 | 64.1 ± 10.0 | 62.3 ± 11.3 | 67.4 ± 9.2 |
| Epiglottis | 65.5 ± 8.6 | 65.5 ± 11.0 | 65.4 ± 13.1 | 67.3 ± 8.2 |
| Esophagus | 66.3 ± 23.2 | 61.6 ± 12.0 | 69.1 ± 12.9 | 67.0 ± 14.0 |
| Eye Lt | 83.4 ± 7.4 | 86.4 ± 3.4 | 85.7 ± 7.4 | 86.4 ± 3.3 |
| Eye Rt | 82.7 ± 6.3 | 85.9 ± 3.3 | 86.7 ± 4.3 | 86.6 ± 4.0 |
| Hippocampus Lt | 62.4 ± 12.5 | 46.2 ± 17.3 | 50.0 ± 17.3 | 67.4 ± 16.0 |
| Hippocampus Rt | 62.2 ± 14.3 | 45.2 ± 12.1 | 52.2 ± 17.6 | 67.9 ± 18.9 |
| Hypothalamus | 63.6 ± 17.3 | 39.2 ± 16.8 | 28.7 ± 22.9 | 72.6 ± 17.1 |
| Inner ear Lt | 62.4 ± 12.1 | 58.4 ± 10.6 | 68.8 ± 10.9 | 78.8 ± 8.1 |
| Inner ear Rt | 63.2 ± 16.8 | 60.1 ± 10.3 | 73.0 ± 12.2 | 76.9 ± 9.1 |
| Lacrimal gland Lt | 59.2 ± 10.5 | 54.7 ± 11.5 | 64.1 ± 16.0 | 70.7 ± 8.0 |
| Lacrimal gland Rt | 58.7 ± 10.5 | 54.7 ± 11.5 | 52.1 ± 14.3 | 70.6 ± 11.0 |
| Larynx core | 57.9 ± 17.1 | 53.9 ± 17.1 | 56.9 ± 20.1 | 69.7 ± 20.8 |
| Mandible Lt | 87.4 ± 2.9 | 90.2 ± 2.0 | 88.2 ± 12.1 | 91.7 ± 1.8 |
| Mandible Rt | 89.1 ± 2.3 | 90.8 ± 1.8 | 88.0 ± 6.0 | 91.1 ± 2.5 |
| Optic Chiasm | 49.9 ± 15.4 | 50.9 ± 13.6 | 60.4 ± 22.1 | 72.9 ± 9.2 |
| Optic Nerve Lt | 61.7 ± 11.1 | 67.6 ± 11.0 | 69.9 ± 9.3 | 74.3 ± 7.8 |
| Optic Nerve Rt | 62.0 ± 12.2 | 67.6 ± 10.2 | 69.9 ± 11.0 | 72.3 ± 8.7 |
| Oral cavity | 64.0 ± 5.1 | 76.3 ± 5.1 | 77.8 ± 10.2 | 82.6 ± 5.3 |
| Parotid Lt | 64.7 ± 5.8 | 78.2 ± 5.1 | 82.8 ± 6.2 | 84.5 ± 4.2 |
| Parotid Rt | 64.7 ± 6.1 | 78.8 ± 6.5 | 82.3 ± 6.6 | 84.1 ± 5.0 |
| Pineal Gland | 46.4 ± 29.3 | 60.2 ± 16.5 | 63.6 ± 26.4 | 70.4 ± 14.7 |
| Pituitary | 60.4 ± 11.0 | 65.2 ± 11.0 | 57.0 ± 14.8 | 61.5 ± 18.4 |
| Spinal cord | 83.5 ± 6.2 | 83.7 ± 3.6 | 82.7 ± 7.4 | 84.6 ± 2.4 |
| SMG Lt | 64.2 ± 16.8 | 71.3 ± 8.8 | 77.3 ± 9.1 | 76.9 ± 9.8 |
| SMG Rt | 63.2 ± 16.8 | 69.5 ± 11.7 | 75.2 ± 9.4 | 76.1 ± 9.0 |
| Temporal Lobe Lt | 66.7 ± 3.6 | 80.9 ± 3.7 | 82.6 ± 6.4 | 81.0 ± 5.2 |
| Temporal Lobe Rt | 65.1 ± 5.1 | 73.6 ± 17.4 | 82.4 ± 5.7 | 80.5 ± 4.0 |
| Thyroid Lt | 64.9 ± 18.9 | 76.7 ± 7.7 | 81.2 ± 6.1 | 81.6 ± 5.0 |
| Thyroid Rt | 64.4 ± 17.7 | 77.0 ± 6.0 | 80.5 ± 10.5 | 82.2 ± 5.1 |
| TM joint Lt | 79.2 ± 6.5 | 77.2 ± 6.5 | 79.3 ± 12.8 | 77.6 ± 7.0 |
| TM joint Rt | 76.5 ± 8.8 | 75.2 ± 9.3 | 77.4 ± 9.6 | 76.2 ± 7.1 |
| Average | 66.6 | 67.6 | 70.4 | 75.1 |

TABLE 8

| Organ | UNet | P-HNN | UaNet | SOARS |
|---|---|---|---|---|
| Basal Ganglia Lt | 10.0 ± 2.8 | 9.8 ± 3.2 | 10.5 ± 4.0 | 9.3 ± 3.2 |
| Basal Ganglia Rt | 9.3 ± 3.8 | 10.2 ± 3.3 | 10.5 ± 3.8 | 11.1 ± 3.4 |
| Brachial Lt | 14.9 ± 6.2 | 15.1 ± 9.6 | 14.2 ± 11.7 | 17.3 ± 10.9 |
| Brachial Rt | 17.9 ± 8.2 | 11.4 ± 5.0 | 16.2 ± 9.6 | 14.0 ± 7.3 |
| Brainstem | 8.4 ± 2.9 | 8.8 ± 2.9 | 10.3 ± 3.8 | 8.1 ± 2.2 |
| Cerebellum | 8.9 ± 3.8 | 9.4 ± 4.7 | 14.1 ± 9.8 | 7.7 ± 3.1 |
| Cochlea Lt | 3.6 ± 9.0 | 1.8 ± 0.5 | 2.3 ± 0.8 | 1.6 ± 0.4 |
| Cochlea Rt | 2.1 ± 0.8 | 2.0 ± 1.0 | 2.4 ± 0.9 | 1.9 ± 0.6 |
| Const. inf | 5.7 ± 2.6 | 8.5 ± 3.9 | 7.5 ± 4.9 | 5.4 ± 2.4 |
| Const. mid | 7.4 ± 2.8 | 8.7 ± 3.1 | 14.7 ± 10.1 | 7.4 ± 3.3 |
| Const. sup | 7.4 ± 3.0 | 8.0 ± 3.6 | 12.7 ± 8.2 | 7.0 ± 3.6 |
| Epiglottis | 6.7 ± 2.3 | 6.9 ± 3.6 | 9.9 ± 8.5 | 6.9 ± 2.5 |
| Esophagus | 25.1 ± 26.4 | 21.9 ± 13.7 | 24.0 ± 15.0 | 21.1 ± 15.8 |
| Eye Lt | 2.8 ± 0.8 | 3.0 ± 1.8 | 4.0 ± 5.4 | 3.3 ± 1.1 |
| Eye Rt | 3.1 ± 0.9 | 3.4 ± 0.9 | 3.1 ± 0.7 | 3.0 ± 1.0 |
| Hippocampus Lt | 11.0 ± 6.7 | 16.9 ± 8.6 | 15.9 ± 8.9 | 12.2 ± 7.7 |
| Hippocampus Rt | 10.7 ± 6.1 | 12.7 ± 5.8 | 13.3 ± 6.6 | 12.5 ± 8.2 |
| Hypothalamus | 16.9 ± 8.6 | 9.3 ± 4.3 | 10.3 ± 3.7 | 2.5 ± 1.3 |
| Inner ear Lt | 12.7 ± 5.8 | 11.9 ± 33.7 | 4.0 ± 1.4 | 2.6 ± 0.7 |
| Inner ear Rt | 9.3 ± 4.3 | 4.1 ± 1.3 | 4.7 ± 2.8 | 2.9 ± 0.8 |
| Lacrimal Gland Lt | 4.3 ± 1.0 | 4.3 ± 1.3 | 4.6 ± 1.6 | 2.9 ± 1.1 |
| Lacrimal Gland Rt | 4.1 ± 1.2 | 5.5 ± 1.5 | 5.1 ± 2.2 | 2.9 ± 0.9 |
| Larynx core | 12.4 ± 7.3 | 10.4 ± 7.3 | 9.2 ± 7.2 | 9.0 ± 7.1 |
| Mandible Lt | 7.9 ± 2.9 | 6.7 ± 2.8 | 10.3 ± 24.4 | 5.3 ± 2.3 |
| Mandible Rt | 7.0 ± 2.6 | 5.6 ± 2.3 | 12.2 ± 15.8 | 5.5 ± 1.6 |
| Optic Chiasm | 8.0 ± 3.9 | 8.4 ± 5.3 | 11.4 ± 7.8 | 5.3 ± 4.2 |
| Optic Nerve Lt | 4.2 ± 3.6 | 4.6 ± 3.5 | 5.2 ± 3.1 | 3.4 ± 1.9 |
| Optic Nerve Rt | 4.1 ± 2.3 | 3.9 ± 1.7 | 4.9 ± 4.2 | 3.3 ± 1.4 |
| Oral cavity | 16.4 ± 5.0 | 18.4 ± 5.0 | 7.6 ± 10.3 | 13.8 ± 6.2 |
| Parotid Lt | 9.0 ± 3.4 | 10.0 ± 2.8 | 8.0 ± 5.8 | 7.0 ± 2.5 |
| Parotid Rt | 8.9 ± 7.8 | 8.3 ± 2.0 | 9.7 ± 4.2 | 6.8 ± 1.6 |
| Pineal Gland | 3.4 ± 1.8 | 2.5 ± 1.1 | 4.0 ± 1.9 | 1.7 ± 0.6 |
| Pituitary | 3.9 ± 1.4 | 4.4 ± 1.6 | 4.4 ± 1.3 | 4.2 ± 2.2 |
| Spinal cord | 34.9 ± 13.9 | 10.2 ± 18.1 | 17.3 ± 27.2 | 5.7 ± 2.2 |
| SMG Lt | 7.3 ± 4.0 | 18.6 ± 30.3 | 6.1 ± 5.4 | 6.5 ± 3.1 |
| SMG Rt | 7.3 ± 4.0 | 11.1 ± 8.3 | 7.0 ± 4.9 | 6.1 ± 2.3 |
| Temporal Lobe Lt | 14.3 ± 21.4 | 16.0 ± 6.8 | 16.5 ± 6.7 | 14.6 ± 6.9 |
| Temporal Lobe Rt | 12.8 ± 3.6 | 38.6 ± 85.2 | 15.0 ± 5.0 | 13.5 ± 5.9 |
| Thyroid Lt | 9.0 ± 2.9 | 6.9 ± 3.2 | 7.4 ± 4.8 | 5.1 ± 2.5 |
| Thyroid Rt | 8.7 ± 10.4 | 7.9 ± 3.3 | 7.1 ± 4.0 | 5.5 ± 2.3 |
| TM joint Lt | 3.5 ± 1.2 | 3.9 ± 1.4 | 4.4 ± 2.4 | 3.6 ± 1.7 |
| TM joint Rt | 3.6 ± 1.7 | 4.6 ± 1.1 | 4.3 ± 2.9 | 3.5 ± 1.3 |
| Anchor OARs | 9.3 | 9.4 | 9.2 | 7.0 |

MICCAI2015 dataset was used as an external dataset to further demonstrate the generalizability of SOARS. Similar to previous comparison methods, the disclosed framework were trained from scratch using only MICCAI2015 training set, and get an average DSC of 82.4%, which is an 1.2% improvement compared to Tong et al., or 2.1% over Gao et al. Table 9 reports comparison results with competitor methods. As shown in Table 9, the disclosed SOARS achieved 7 best performance and 2 second best performance on all 9 OARs. The most difficult organ in segmentation task is optic chiasm, where the disclosed SOARS have a 3.4% improvement on DSC as compared to the best previous result achieved by UaNet. This validates the effectiveness and consistency of the disclosed method.

TABLE 9

| | | Ren et al. | Wang et al. | PHNN | Anatomy Net | Focus Net | UaNet | SOARS |
|---|---|---|---|---|---|---|---|---|
| Brain Stem | | — | — | 90.0 ± 4.0 | 87.2 ± 2.5 | 86.7 ± 2.0 | 87.5 ± 2.6 | 87.5 ± 2.5 | 87.6 ± 2.8 |
| Mandible | | — | — | 94.0 ± 1.0 | 93.1 ± 1.8 | 92.5 ± 2.0 | 93.5 ± 1.9 | 95.0 ± 0.8 | 95.1 ± 1.1 |
| Optic Chiasm | | — | 58.0 ± 17.0 | — | 55.6 ± 14.1 | 53.2 ± 15.0 | 59.6 ± 18.1 | 61.5 ± 10.2 | 64.9 ± 8.8 |
| Optic | Lt | 72.0 ± 8.0 | — | 72.6 ± 4.6 | 72.1 ± 6.0 | 73.5 ± 9.6 | 74.8 ± 7.1 | 75.3 ± 7.1 |
| Nerve | Rt | 70.0 ± 90 | — | 71.2 ± 4.4 | 70.6 ± 10.0 | 74.4 ± 7.2 | 72.3 ± 5.9 | 74.6 ± 5.2 |
| Parotid | Lt | — | 83.0 ± 6.0 | 87.7 ± 1.8 | 88.1 ± 2.0 | 86.3 ± 3.6 | 88.7 ± 1.9 | 88.2 ± 3.2 |
| | Rt | — | 83.0 ± 6.0 | 87.8 ± 2.3 | 87.3 ± 4.0 | 87.9 ± 3.1 | 87.5 ± 5.0 | 88.2 ± 5.2 |
| SMG | Lt | — | — | 80.6 ± 5.5 | 81.4 ± 4.0 | 79.8 ± 8.1 | 82.3 ± 5.2 | 84.2 ± 7.3 |
| | Rt | — | — | 80.7 ± 6.1 | 81.3 ± 4.0 | 80.1 ± 6.1 | 81.5 ± 4.5 | 83.8 ± 6.9 |
| All OARs | | — | — | 79.6 | 79.2 | 80.3 | 81.2 | 82.4 |

Previous works on OARs segmentation include atlas-based approaches, statistical shape or appearance models, and neural network based approaches. The main disadvantage of atlas-based approaches is reliance on accurate and efficient image registration, which is challenged by shape variations, normal tissue removal, abnormal tissue growth, and image acquisition differences, and also take long time to complete. The issue of statistical models is that they can be limited to specific shapes described by the statistical model, which makes them less flexible when the number of OARs is large. Recently, deep NN based approaches, such as fully convolutional networks (FCNs), have proven capable of delivering substantially better performance. have quickly become the mainstream method. FocusNet and UaNet do not stratify OARs, and hence, cannot use easier OARs as support to more difficult ones. Moreover, when the number of OARs is large, e.g. >40, optimization becomes more difficult. Finally, their network architecture remains manually fixed, which is less optimized for the distinct OARs categories Additionally, in existing technologies, network architecture used for organ segmentation are manually crafted and fixed across all the OARs.

In summary, the contribution and novelty of embodiments of the present disclosure are three folds. First, segmenting a comprehensive set of OARs is essential and critical for radiotherapy treatment planning in head and neck cancer. The most clinically complete and desirable set of 42 OARs were used to validate the disclosed method and yield desirable performance result compared to other existing technologies. Second, the disclosed framework focuses on stratifying different organs into different categories of OARs which to be dealt respectively with tailored segmentors (achieved by NAS, which is a well-calibrated framework of integrating organ stratification, multi-stage segmentation and NAS in a synergy. Third, stratifying the to-be-segmented objects into multiple categories or levels may be determined based on field knowledge and sizes of the objects. For example, segmentation of OARs may consult knowledge of oncologists and refer to size distributions of the OARs. The disclosed method and device thus provides an effective image segmentation scheme for image data sets containing multiple objects.

Those skilled in the art should know that: all or part of the steps of the method embodiment may be implemented by related hardware instructed through a program, the program may be stored in a computer-readable storage medium, and the program is executed to execute the steps of the method embodiment; and the storage medium includes: various media capable of storing program codes, such as mobile storage equipment, a Read-Only Memory (ROM), a magnetic disk or a compact disc.

Alternatively, when the integrated unit is implemented in the form of a software functional unit and sold or used as an independent product, the integrated unit may be stored in a computer-readable storage medium. Based on such an understanding, the technical solutions of the present disclosure essentially, or the part contributing to the prior art, or all or some of the technical solutions may be implemented in the form of a software product. The software product is stored in a storage medium and includes several instructions for instructing a computer device (which may be a personal computer, a server, or a network device) to perform all or some of the steps of the methods described in the embodiments of the present disclosure. The foregoing storage medium includes: any medium that can store program code, such as a USB flash drive, a removable hard disk, a read-only memory (ROM), a random access memory (RAM), a magnetic disk, or an optical disc.

Other embodiments of the disclosure will be apparent to those skilled in the art from consideration of the specification and practice of the invention disclosed herein. It is intended that the specification and examples be considered as exemplary only, with a true scope and spirit of the invention being indicated by the claims.

What is claimed is:

1. A method for stratified image segmentation, comprising:
    obtaining a three-dimensional (3D) image data set representative of a region comprising at least three levels of objects;
    generating a first segmentation result indicating boundaries of anchor-level objects in the region based on a first neural network (NN) model corresponding to the anchor-level objects;
    generating a second segmentation result indicating boundaries of mid-level objects in the region based on the first segmentation result and a second NN model corresponding to the mid-level objects; and
    generating a third segmentation result indicating small-level objects in the region based on the first segmentation result, a third NN model corresponding to the small-level objects, and cropped regions corresponding to the small-level objects, wherein generating the third segmentation result comprises: for each small-level object,
    detecting a center region of the small-level object based on the first segmentation result and the 3D image data set;
    determining a volume of interest (VOI) within the 3D image data set based on the center region of the small-level object; and
    segmenting the small-level object from the VOI using the third NN model.

2. The method according to claim 1, wherein the image data, set comprises a plurality of voxels, and each voxel corresponds to a vector valued mask that provides a probability of the voxel belonging to each of the multiple objects according to the first, second, and third segmentation results.

3. The method according to claim 1, wherein generating the second segmentation result comprises:
    combining location references and semantically-based cues from the first segmentation result to generate the second segmentation result.

4. The method according to claim 1, wherein the center region of the small-level object is detected based on location references provided by the first segmentation result and a heat map regression method based on a fourth NN model.

5. The method according to claim 1, wherein at least one of the first, second, and third NN models is a progressive holistically-nested network model.

6. The method according to claim 1, wherein the first, second, and third NN models are identified through differentiable neural architecture search (NAS).

7. The method according to claim 6, wherein a search space for the NAS includes 2D, 3D, and Pseudo-3D (P3D) convolutions for a first kernel size, and 2D, 3D, and Pseudo-3D (P3D) convolutions for a second kernel size.

8. The method according to claim 1, wherein the 3D image data set is a data set of radiotherapy computed tomography (RTCT) images.

9. The method according to claim 8, wherein the RTCT in ages are scanned from a head and neck region.

10. A device for stratified image segmentation, comprising:
    a memory; and
    a processor coupled to the memory and configured to:
        obtain a three-dimensional (3D) image data set representative of a region comprising at least three levels of objects;

generate a first segmentation result indicating boundaries of anchor-level objects in the region based on a first neural network (NN) model corresponding to the anchor-level objects;

generate a second segmentation result indicating boundaries of mid-level objects in the region based on the first segmentation result and a second NN model corresponding to the mid-level objects; and generate a third segmentation result indicating small-level objects in the region based on the first segmentation result, a third NN model corresponding to the small-level objects, and cropped regions corresponding to the small-level objects, wherein the processor is further configured to: for each small-level object, detect a center region of the small-level object based on the first segmentation result and the 3D image data set;

determine a volume of interest (VOI) within the 3D image data set based on the center region of the small-level object; and segment the small-level object from the VOI using the third NN model.

11. The device according to claim 10, wherein the image data set comprises a plurality of voxels, and each voxel corresponds to a vector valued mask that provides a probability of the voxel belonging to each of the multiple objects according to the first, second, and third segmentation results.

12. The device according to claim 10, wherein for generating the second segmentation result, the processor is further configured to:

combine location references and semantically-based cues from the first segmentation result to generate the second segmentation result.

13. The device according to claim 10, wherein the center region of the all-level object is detected based on location references provided by the first segmentation result and a heat map regression method based on a fourth NN model.

14. The device according to claim 10, wherein at least one of the first, second, and third NN models is a progressive holistically-nested network model.

15. The device according to claim 10, wherein the first, second, and third NN models are identified through differentiable neural architecture search (NAS).

16. The device according to claim 15, wherein a search space for the NAS includes 2D, 3D, and Pseudo-3D (P3D) convolutions for a first kernel size, and 2D, 3D, and Pseudo-3D (P3D) convolutions for a second kernel size.

17. The device according to claim 10, wherein the 3D image data set is a data set of radiotherapy computed tomography (RTCT) images.

18. A non-transitory computer readable storage medium, storing computer instructions that, when being executed by a processor, causing the processor to perform:

obtaining a three-dimensional (3D) image data set representative of a region comprising at least three levels of objects;

generating a first segmentation result indicating boundaries of anchor-level objects in the region based on a first neural network (NN) model corresponding to the anchor-level objects;

generating a second segmentation result indicating boundaries of objects in the region based on the first segmentation result and a second NN model corresponding to the objects; and generating a third segmentation result indicating small-level objects in the region based on the first segmentation result, a third NN model corresponding to the small-level objects, and cropped regions corresponding to the small-level objects, wherein generating the third segmentation result comprises: for each small-level object, detecting a center region of the small-level object based on the first segmentation result and the 3D image data set;

determining a volume of interest (VOI) within the 3D image data set based on the center region of the s all-level object; and segmenting the small-level object from the VOI using the third NN model.

* * * * *